(12) United States Patent
Green et al.

(10) Patent No.: US 9,070,543 B2
(45) Date of Patent: Jun. 30, 2015

(54) ION MOBILITY SEPARATOR WITH VARIABLE EFFECTIVE LENGTH

(71) Applicant: Micromass UK Limited, Wilmslow (GB)

(72) Inventors: Martin Raymond Green, Bowdon (GB); David J. Langridge, Stockport (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 14/479,805

(22) Filed: Sep. 8, 2014

(65) Prior Publication Data

US 2015/0028200 A1    Jan. 29, 2015

Related U.S. Application Data

(63) Continuation of application No. 14/004,486, filed as application No. PCT/GB2012/050545 on Mar. 13, 2012, now Pat. No. 8,829,433.

(60) Provisional application No. 61/476,850, filed on Apr. 19, 2011.

(30) Foreign Application Priority Data

Mar. 14, 2011    (GB) .................................. 1104238.9

(51) Int. Cl.
*B01D 59/44*    (2006.01)
*B01D 59/46*    (2006.01)
(Continued)

(52) U.S. Cl.
CPC .............. *H01J 49/36* (2013.01); *G01N 27/624* (2013.01); *H01J 49/42* (2013.01); *H01J 49/06* (2013.01)

(58) Field of Classification Search
USPC .......................... 250/281–284, 288–294, 297
See application file for complete search history.

(56) References Cited

U.S. PATENT DOCUMENTS

| 6,727,495 B2 | 4/2004 | Li |
| 7,227,132 B2 | 6/2007 | Guervremont et al. |

(Continued)

FOREIGN PATENT DOCUMENTS

| GB | 2457556 | 8/2009 |
| WO | 01/22049 | 3/2001 |
| WO | 2008/071967 | 6/2008 |

OTHER PUBLICATIONS

Loboda, "*Novel Ion Mobility Setup Combined with Collision Cell and Time of Flight Mass Spectrometer*" J. Am Soc. Mass Spectrom., vol. 17, Issue 5, pp. 691-699, 2006.

(Continued)

*Primary Examiner* — Bernard E Souw
(74) *Attorney, Agent, or Firm* — Diederiks & Whitelaw, PLC

(57) ABSTRACT

An ion mobility separator or spectrometer is disclosed comprising an inner cylinder and an outer cylinder defining an annular volume through which ions are transmitted. Spiral electrodes a-f are arranged on a surface of the inner cylinder and/or on a surface of the outer cylinder. A first device is arranged and adapted to maintain a DC electric field and/or a pseudo-potential force which acts to urge ions from a first end of the ion mobility separator or spectrometer to a second end of the ion mobility separator or spectrometer. A second device is arranged and adapted to apply transient DC voltages to the one or more spiral electrodes in order to urge ions towards the first end of the ion mobility separator or spectrometer. The net effect is to extend the effective path length of the ion mobility separator.

20 Claims, 12 Drawing Sheets

(51) Int. Cl.
*B01D 59/50* (2006.01)
*H01J 49/26* (2006.01)
*H01J 49/36* (2006.01)
*G01N 27/62* (2006.01)
*H01J 49/42* (2006.01)
*H01J 49/06* (2006.01)

(56) References Cited

U.S. PATENT DOCUMENTS

| | | |
|---|---|---|
| 7,576,321 B2 | 8/2009 | Wu |
| 7,718,960 B2 | 5/2010 | Hashimoto et al. |
| 8,507,852 B2 * | 8/2013 | Makarov ............... 250/290 |
| 8,829,433 B2 * | 9/2014 | Green et al. ............ 250/290 |
| 2003/0132379 A1 | 7/2003 | Li |
| 2003/0213903 A1 | 11/2003 | Ichimura et al. |
| 2004/0031920 A1 | 2/2004 | Giles et al. |
| 2009/0173877 A1 | 7/2009 | Bateman et al. |
| 2011/0168882 A1 | 7/2011 | Hoyes |
| 2013/0306858 A1 | 11/2013 | Giles et al. |
| 2014/0048695 A1 | 2/2014 | Giles et al. |
| 2014/0124663 A1 * | 5/2014 | Green et al. ............ 250/290 |
| 2014/0145074 A1 | 5/2014 | Giles et al. |

OTHER PUBLICATIONS

Sugai, *"Fundamentals of Mass Spectrometry—Ion Mobility Spectrometry"*, Journal of Mass Spectrometry Society of Japan, vol. 58, No. 2, pp. 47-73, 2010.

* cited by examiner

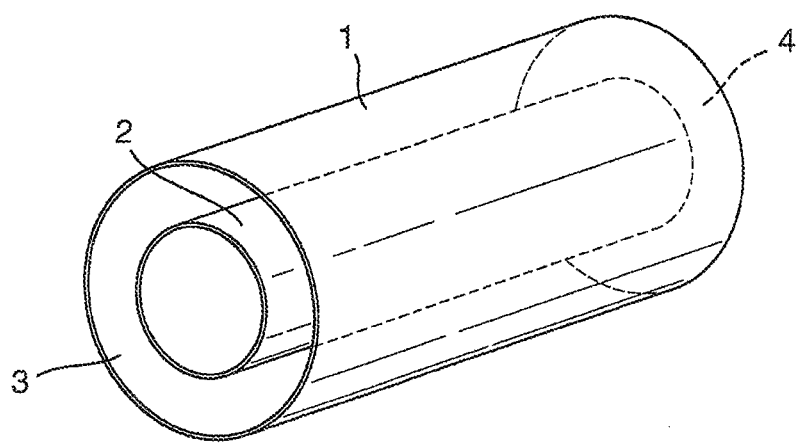
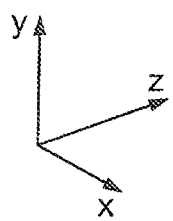

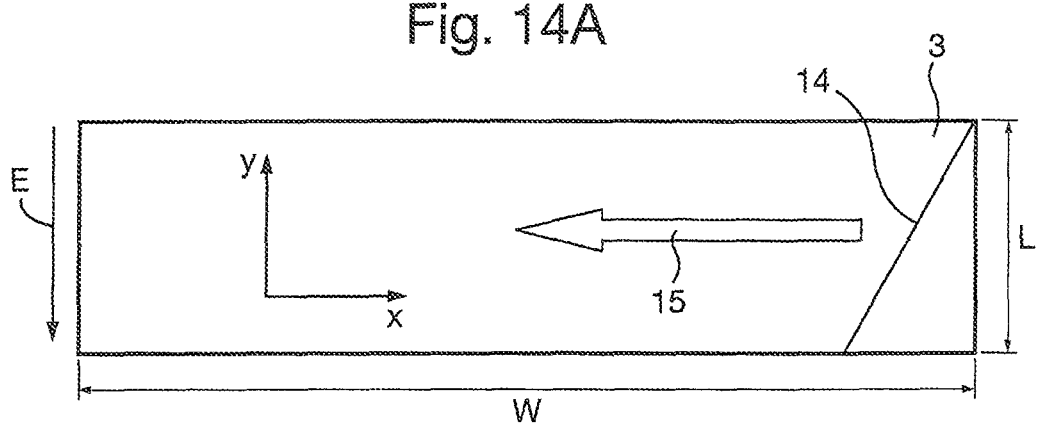
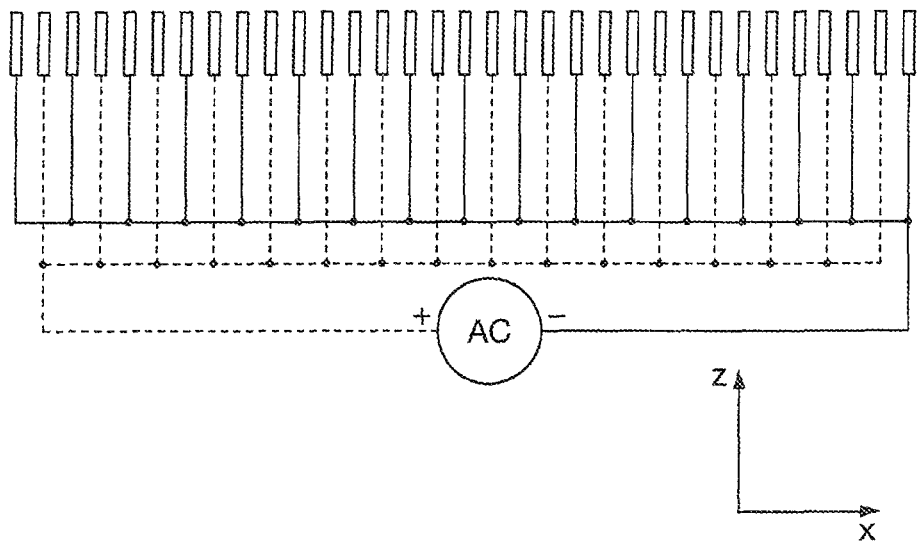

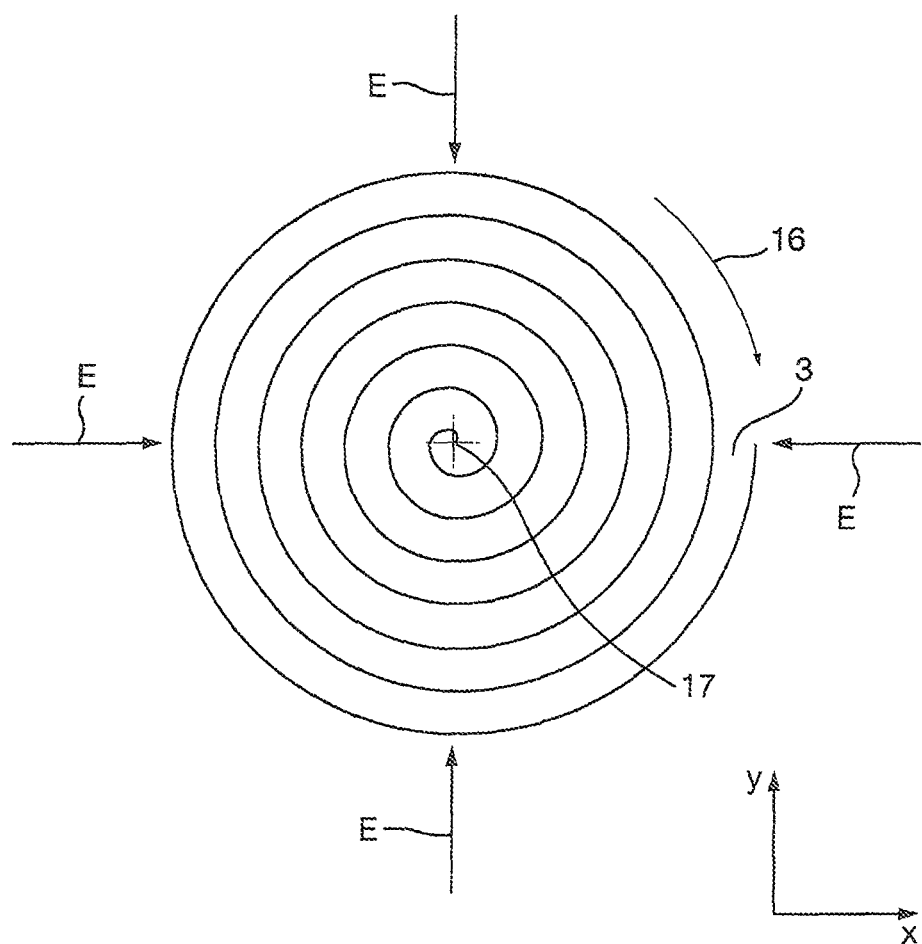

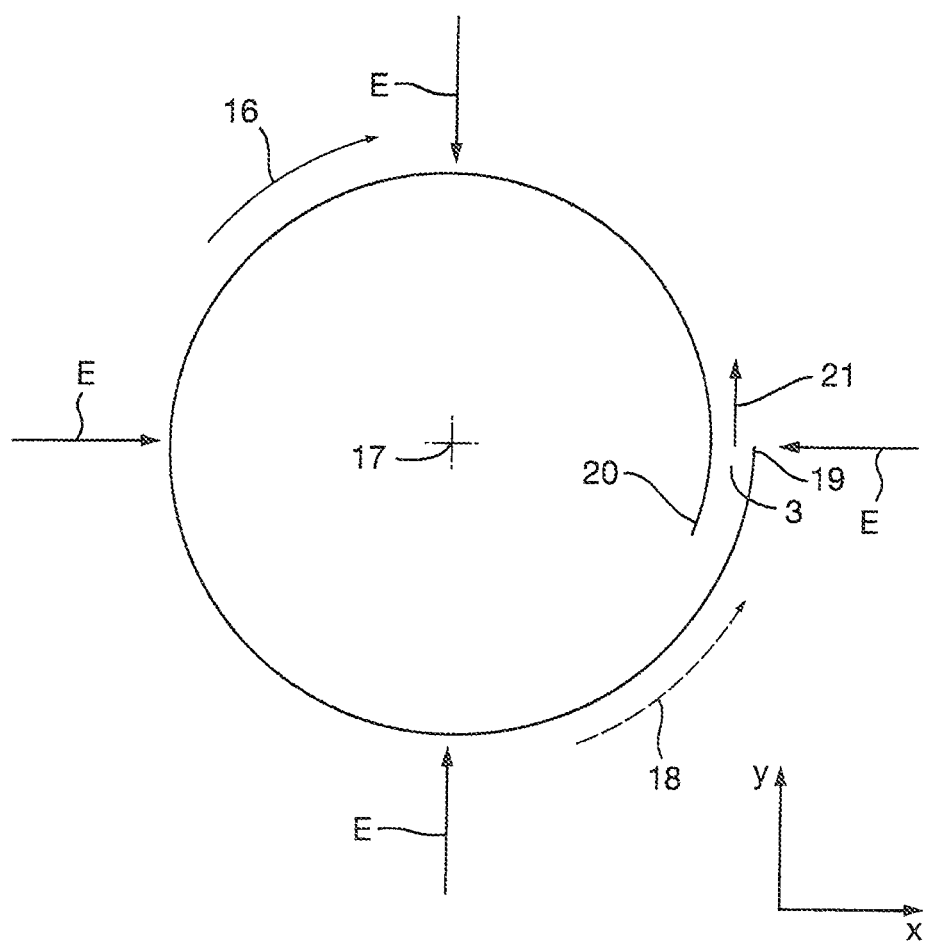

ION MOBILITY SEPARATOR WITH VARIABLE EFFECTIVE LENGTH

CROSS-REFERENCE TO RELATED APPLICATION

This application is a continuation application of U.S. Ser. No. 14/004,486, filed 11 Sep. 2013, which is the National Stage of International Application No. PCT/GB2012/050545, filed 13 Mar. 2012, which claims priority from and the benefit of U.S. Provisional Patent Application Ser. No. 61/476,850 filed on 19 Apr. 2011 and United Kingdom Patent Application No. 1104238.9 filed on 14 Mar. 2011. The entire contents of these applications are incorporated herein by reference.

BACKGROUND TO THE INVENTION

The present invention relates to the field of mass spectrometry and in particular ion mobility spectrometry.

Ion Mobility Spectrometry ("IMS") is a well established analytical technique where ionic species are separated according to their ion mobility by subjecting the ions to a weak electric field in the presence of a buffer gas. A known ion mobility spectrometer comprises a linear tube filled with gas. A static homogeneous axial electric field is maintained along the length of the tube. Ions experience an axial force in one direction due to the electric field and an effective force in the other direction due to collisions with the buffer gas.

The ion mobility resolution R of such a system can be expressed by Eqn. 1:

$$R = \frac{T}{\Delta t} = \frac{K}{\Delta K} = \sqrt{\frac{LEq}{16 \, kT\ln(2)}} \quad (1)$$

wherein L is the length of the tube (m), E is the electric field (V/m), K is Boltzmann's constant, T is the temperature of the buffer gas (K), K is the mobility ($M^2V^{-1}s^{-1}$) and q is the charge on the ion.

To improve ion mobility resolution R the length of the drift tube may be increased or the electric field may be increased. However, the relationship in Eqn. 1 only holds approximately below a low electric field limit wherein the ratio of electric field to buffer gas number density is below a certain value. To allow the field to be increased without exceeding this value requires the pressure to be increased by the same factor. Both these approaches lead to practical limitations in the IMS resolution which can ultimately be achieved.

Another approach to increasing IMS resolution without increasing path length is described in Novel Ion Mobility Setup Combined with Collision Cell and Time of Flight Mass Spectrometer, J. Am Soc Mass Spectrom, 2006, Volume 17, Issue 5, p 691-699, Alexander Loboda. In this method the buffer gas is allowed to flow in a direction opposing the electric field. The combination of gas flow and DC field allow ions to remain longer in the cell thereby experiencing more collisions with the buffer gas. This results in marked improvements in mobility resolution without increasing the physical length of the mobility device. Careful design of the gas flow dynamics of the IMS cell must be considered in this approach to avoid turbulent flow effects which will cause a degrading of IMS resolution.

It is desired to provide an improved mass spectrometer and method of mass spectrometry.

SUMMARY OF THE INVENTION

According to an aspect of the present invention there is provided apparatus for separating ions according to one or more physico-chemical properties, wherein the apparatus is arranged and adapted to create an ion channel in which ions are confined in use and wherein the ions are caused to separate according to the one or more physico-chemical properties along an axis of the ion channel or along the ion channel towards a first end and wherein the apparatus is further arranged and adapted to move the axis of the ion channel or the ion channel away from the first end.

According to the preferred embodiment the axis of the ion channel and/or the ion channel is non-linear. For example, the axis of the ion channel and/or the ion channel may be helical, spiral or curved.

According to a less preferred embodiment the axis of the ion channel and/or the ion channel may be linear.

According to the preferred embodiment the first end comprises an exit and is opposed to a second end through which ions initially entered the apparatus i.e. ions travel from an ion entrance to an ion exit through the apparatus. However, according to a less preferred embodiment the first end may comprise an entrance through which ions initially entered the apparatus. According to this embodiment the direction in which ions come out of or exit the apparatus can be reversed by moving the ion channel faster than the velocity of a particular ion.

The effect of moving the axis of the ion channel or the ion channel away from the exit is to increase the effective path length along which ions separate according to the one or more physico-chemical properties.

The ion channel preferably comprises a DC potential well.

The ion channel is preferably formed between: (i) a first DC voltage gradient, a first DC potential, a first electrostatic barrier, a first DC potential barrier or a first pseudo-potential; and (ii) a second moving DC potential barrier, a second moving electrostatic barrier, a second moving DC potential barrier or a second moving pseudo-potential barrier.

Ions are preferably confined within the ion channel in a first plane or direction by DC voltages, DC potentials or electrostatic potentials.

Ions are preferably confined within the ion channel in a second plane or direction by RF voltages, RF potentials or pseudo-potentials, wherein the second plane or direction is substantially orthogonal to the first plane or direction.

The apparatus preferably comprises:

a first device arranged and adapted to cause ions to separate according to the one or more physico-chemical properties in a first direction or along the axis of the ion channel or along the ion channel with a velocity which is substantially dependent upon the one or more physico-chemical properties.

The first device is preferably arranged and adapted to apply or maintain a first electrostatic potential or force, a first DC potential or force, or a first pseudo-potential or force along at least a portion of the apparatus or along the axis of the ion channel or along the ion channel in order to cause ions to separate according to the one or more physico-chemical properties.

The first device is preferably arranged and adapted to apply or maintain a first electrostatic potential or force, a first DC potential or force, or a first pseudo-potential or force along at least a portion of the apparatus or along the axis of the ion channel or along the ion channel in order to cause ions to separate according to the one or more physico-chemical properties.

The first device is preferably arranged and adapted:

(i) to maintain a first DC voltage gradient, a first DC potential or a first DC electric field across at least a portion or at least 10%, 20%, 30%, 40%, 50%, 60%, 70%, 80% or 90% of the axial length of the apparatus or along the axis of the ion channel or along the ion channel; and/or (ii) to apply a first electrostatic potential or force along at least a portion or at least 10%, 20%, 30%, 40%, 50%, 60%, 70%, 80% or 90% of the axial length of the apparatus or along the axis of the ion channel or along the ion channel; and/or (iii) to apply one or more first transient DC voltages or potentials to a plurality of electrodes in order to urge ions along at least a portion or at least 10%, 20%, 30%, 40%, 50%, 60%, 70%, 80% or 90% of the axial length of the apparatus or along the axis of the ion channel or along the ion channel; and/or (iv) to apply a first RF voltage comprising three or more phases to a plurality of electrodes, wherein different electrodes are connected to different phases of the RF voltage and wherein the first RF voltage urges ions along at least a portion or at least 10%, 20%, 30%, 40%, 50%, 60%, 70%, 80% or 90% of the axial length of the apparatus or along the axis of the ion channel or along the ion channel; and/or (v) to apply a first pseudo-potential or force wherein the amplitude and/or frequency of an RF voltage applied to a plurality of electrodes varies, increases or decreases along at least a portion or at least 10%, 20%, 30%, 40%, 50%, 60%, 70%, 80% or 90% of the axial length of the apparatus or along the axis of the ion channel or along the ion channel.

The apparatus preferably further comprises a second device arranged and adapted to drive the ions in a second direction with a velocity which is substantially independent of the one or more physico-chemical properties.

The second device is preferably arranged and adapted to apply or maintain a second moving electrostatic potential barrier, a second moving DC potential barrier or a second moving pseudo-potential barrier along at least a portion of the apparatus in order to drive the ions in the second direction.

The first electrostatic potential or force, the first DC potential or force, or the first pseudo-potential or force is preferably substantially greater than, equal to, or less than the second moving electrostatic potential barrier, the second moving DC potential barrier or the second moving pseudo-potential barrier.

The second device is preferably arranged and adapted:

(i) to apply a second moving electrostatic potential barrier along at least a portion or at least 10%, 20%, 30%, 40%, 50%, 60%, 70%, 80% or 90% of the axial length of the apparatus; and/or (ii) to apply one or more second transient DC voltages or potentials to a plurality of electrodes in order to urge ions along at least a portion or at least 10%, 20%, 30%, 40%, 50%, 60%, 70%, 80% or 90% of the axial length of the apparatus; and/or (iii) to apply a second RF voltage comprising three or more phases to a plurality of electrodes, wherein different electrodes are connected to different phases of the RF voltage and wherein the second RF voltage urges ions along at least a portion or at least 10%, 20%, 30%, 40%, 50%, 60%, 70%, 80% or 90% of the axial length of the apparatus; and/or (iv) to apply a second moving pseudo-potential barrier wherein the amplitude and/or frequency of an RF voltage applied to a plurality of electrodes varies, increases or decreases along at least a portion or at least 10%, 20%, 30%, 40%, 50%, 60%, 70%, 80% or 90% of the axial length of the apparatus.

According to an embodiment:

(i) the first electrostatic potential or force is substantially greater than, equal to, or less than the second moving electrostatic potential barrier; and/or (ii) the first DC potential or the first DC electric field is substantially greater than, equal to, or less than the second moving DC potential barrier;

(iii) the first transient DC voltages or potentials have an amplitude which is substantially greater than, equal to or less than the second transient DC voltages or potentials; and/or (iv) the first RF voltage has an amplitude which is substantially greater than, equal to or less than the second RF voltage; and/or (v) the first pseudo-potential or force is substantially greater than, equal to, or less than the second pseudo-potential barrier.

The first device is preferably arranged and adapted to drive or urge ions in the first direction with a first velocity or a first component of velocity and the second device is preferably arranged and adapted to drive or urge ions in the second direction with a second velocity or second component of velocity, wherein the first velocity or first component of velocity is substantially greater than, equal to or less than the second velocity or the second component of velocity.

The first electrostatic potential or force, the first DC potential or force, or the first pseudo-potential or force preferably has a non-zero component:

(i) in a direction which is substantially parallel to the second moving electrostatic potential barrier, the second moving DC potential barrier, or the second moving pseudo-potential barrier at a particular instance in time; and/or (ii) in a direction substantially orthogonal to a direction of movement of the second moving electrostatic potential barrier, the second moving DC potential barrier, or the second moving pseudo-potential barrier.

According to an embodiment the first device drives ions with a first velocity or force in the first direction and the second device drives ions with a second velocity or force in the second direction, wherein either:

(i) the first direction is inclined to or offset relative to the second direction; and/or (ii) the first direction is not co-directional with the second direction; and/or (iii) the first direction is not counter to the second direction; and/or (iv) the first velocity or force has a non-zero component of velocity or force in a direction substantially orthogonal to the second direction.

The first device preferably drives ions with a first velocity or force and the second device drives ions with a second velocity or force, wherein either the first velocity or force and/or the second velocity or force varies with time and/or position.

According to the preferred embodiment the physico-chemical property comprises ion mobility. The apparatus preferably comprises an ion mobility spectrometer or separator.

According to a less preferred embodiment the physico-chemical property comprises differential ion mobility. According to a less preferred embodiment the apparatus comprises a differential ion mobility spectrometer or a Field Asymmetric Ion Mobility Spectrometer ("FAIMS") device.

According to a less preferred embodiment the physico-chemical property comprises mass or mass to charge ratio. The apparatus may comprise a mass or mass to charge ratio analyser.

According to an embodiment the apparatus comprises:

an inner cylinder and an outer cylinder, wherein the inner cylinder and the outer cylinder define an annular volume through which ions are transmitted in use; and wherein one or more spiral or helical electrodes are arranged on a surface of the inner cylinder and/or on a surface of the outer cylinder.

A first device is preferably arranged and adapted to maintain a DC electric field and/or a pseudo-potential force which acts to urge ions from a first end of the apparatus to a second end of the apparatus; and a second device is preferably arranged and adapted to apply one or more transient DC voltages to the one or more spiral or helical electrodes in order to urge ions towards the first end of the apparatus.

The inner cylinder and/or the outer cylinder preferably have a circular, elliptical, non-circular, rectangular or irregular cross section.

The pitch of the one or more spiral or helical electrodes is preferably constant, increases, decreases or varies along the length of the apparatus.

According to an embodiment the apparatus further comprises a device for applying an RF voltage to the one or more spiral or helical electrodes in order to confine ions radially within the annular volume.

The apparatus preferably further comprises a device arranged and adapted to supply a buffer gas to the annular volume between the outer cylinder and the inner cylinder.

The inner cylinder and/or the outer cylinder may comprise a non-conductive or dielectric material.

The apparatus may further comprise one or more auxiliary electrodes provided on an opposite side of the inner cylinder and/or the outer cylinder to that of the one or more spiral or helical electrodes.

An RF voltage may be applied to the one or more auxiliary electrodes.

In a mode of operation ions are preferably urged along a spiral or helical path through the apparatus.

Ions are preferably arranged to enter the apparatus via the annular volume and/or via an aperture in the inner cylinder and/or via an aperture in the outer cylinder.

Ions are preferably separated temporally according to their ion mobility or according to their rate of change of ion mobility with electric field strength.

According to an embodiment:

the apparatus further comprises a plurality of segmented planar electrodes; and a second device arranged and adapted to apply DC voltages to the segmented planar electrodes so that one or more diagonal or inclined DC voltage barriers are translated along at least a portion of the length of the apparatus.

According to an embodiment:

the apparatus further comprises a plurality of inner ring electrodes and a plurality of outer ring electrodes, wherein the inner ring electrodes and the outer ring electrodes define an annular volume through which ions are transmitted in use, wherein the plurality of inner ring electrodes and/or the plurality of outer ring electrodes are radially segmented into a plurality of segmented electrodes.

The first device and the second device are preferably operated at substantially the same time so that the net effect is to extend the path length of ions passing through the apparatus.

According to an aspect of the present invention there is provided a mass spectrometer comprising apparatus as described above.

According to an aspect of the present invention there is provided a method of separating ions according to one or more physico-chemical properties, comprising:

creating an ion channel in which ions are confined and causing the ions to separate according to the one or more physico-chemical properties along an axis of the ion channel or along the ion channel towards a first end; and moving the axis of the ion channel or the ion channel away from the first end.

According to an aspect of the present invention there is provided apparatus for separating ions according to one or more physico-chemical properties comprising:

a plurality of electrodes;

a first device arranged and adapted to cause ions to separate according to the one or more physico-chemical properties in a first direction with a velocity which is substantially dependent upon the one or more physico-chemical properties; and a second device arranged and adapted to drive the ions in a second direction with a velocity which is substantially independent of the one or more physico-chemical properties.

According to an aspect of the present invention there is provided a method of separating ions according to one or more physico-chemical properties comprising:

causing ions to separate according to the one or more physico-chemical properties in a first direction with a velocity which is substantially dependent upon the one or more physico-chemical properties; and driving the ions in a second direction with a velocity which is substantially independent of the one or more physico-chemical properties.

Ions are preferably caused to separate according to the one or more physico-chemical properties in the first direction at substantially the same time that they are driven in the second direction so that the net effect is to extend the path length of ions.

According to an aspect of the present invention there is provided an ion mobility separator comprising:

a first device arranged and adapted to apply or maintain a first electrostatic potential or field, a first DC potential or field, or a first pseudo-potential or field in a first direction so as to cause ions to separate according to their ion mobility in the first direction; and a second device arranged and adapted to drive the ions in a second direction by driving the ions with a second moving electrostatic potential barrier, a second moving DC potential barrier, or a second moving pseudo-potential barrier;

wherein ions are separated according to their ion mobility: (i) in a direction substantially parallel to the second moving electrostatic potential barrier, the second moving DC potential barrier, or the second moving pseudo-potential barrier at a particular instance in time; and/or (ii) in a direction substantially orthogonal to a direction of movement of the second moving electrostatic potential barrier, the second moving DC potential barrier, or the second moving pseudo-potential barrier.

The first device is preferably arranged and adapted to drive or urge the ions in the first direction with a first component of velocity and the second device is preferably arranged and adapted to drive or urge ions in the second direction with a second component of velocity, wherein the first component of velocity is substantially greater than the second component of velocity.

The first electrostatic potential or force, the first DC potential or force, or the first pseudo-potential or force preferably has a non-zero component:

(i) in a direction which is substantially parallel to the second moving electrostatic potential barrier, the second moving DC potential barrier, or the second moving pseudo-potential barrier at a particular instance in time; and/or (ii) in a direction substantially orthogonal to a direction of movement of the second moving electrostatic potential barrier, the second moving DC potential barrier, or the second moving pseudo-potential barrier.

According to an aspect of the present invention there is provided a method of separating ions according to their ion mobility comprising:

applying or maintaining a first electrostatic potential or field, a first DC potential or field, or a first pseudo-potential or field in a first direction so as to cause ions to separate according to their ion mobility in the first direction; and driving the ions in a second direction by driving the ions with a second moving electrostatic potential barrier, a second moving DC potential barrier, or a second moving pseudo-potential barrier;

wherein ions are separated according to their ion mobility: (i) in a direction substantially parallel to the second moving electrostatic potential barrier, the second moving DC potential barrier, or the second moving pseudo-potential barrier at a particular instance in time; and/or (ii) in a direction substantially orthogonal to a direction of movement of the second moving electrostatic potential barrier, the second moving DC potential barrier, or the second moving pseudo-potential barrier.

The method preferably further comprises driving or urging the ions in the first direction with a first component of velocity and simultaneously driving or urging the ions in the second direction with a second component of velocity, wherein the first component of velocity is substantially greater than the second component of velocity.

The first electrostatic potential or force, the first DC potential or force, or the first pseudo-potential or force preferably has a non-zero component:

(i) in a direction which is substantially parallel to the second moving electrostatic potential barrier, the second moving DC potential barrier, or the second moving pseudo-potential barrier at a particular instance in time; and/or (ii) in a direction substantially orthogonal to a direction of movement of the second moving electrostatic potential barrier, the second moving DC potential barrier, or the second moving pseudo-potential barrier.

According to an aspect of the present invention there is provided an ion mobility separator for separating ions according to their ion mobility comprising:

a device arranged and adapted to create a DC ion channel in which ions are confined by DC potentials and wherein the ions are caused to separate according to their ion mobility along an axis of the ion channel or along the ion channel towards an exit of the ion mobility separator; and a device arranged and adapted to move the axis of the ion channel or the ion channel away from the exit thereby increasing the effective path length of the ion mobility separator.

According to an aspect of the present invention there is provided a method of separating ions according to their ion mobility comprising:

creating a DC ion channel in which ions are confined by DC potentials and wherein the ions are caused to separate according to their ion mobility along an axis of the ion channel or along the ion channel towards an exit of the ion mobility separator; and moving the axis of the ion channel or the ion channel away from the exit thereby increasing the effective path length of the ion mobility separator.

According to an aspect of the present invention there is provided an ion mobility separator or spectrometer comprising:

an inner cylinder and an outer cylinder, wherein the inner cylinder and the outer cylinder define an annular volume through which ions are transmitted in use;

one or more spiral electrodes arranged on a surface of the inner cylinder and/or on a surface of the outer cylinder;

a first device arranged and adapted to maintain a DC electric field and/or a pseudo-potential force which acts to urge ions from a first end of the ion mobility separator or spectrometer to a second end of the ion mobility separator or spectrometer; and a second device arranged and adapted to apply one or more transient DC voltages to the one or more spiral electrodes in order to urge ions towards the first end of the ion mobility separator or spectrometer.

According to an aspect of the present invention there is provided a method of separating ions according to their ion mobility comprising:

providing an inner cylinder and an outer cylinder, wherein the inner cylinder and the outer cylinder define an annular volume through which ions are transmitted in use;

providing one or more spiral electrodes arranged on a surface of the inner cylinder and/or on a surface of the outer cylinder;

maintaining a DC electric field which acts to urge ions from a first end of the ion mobility separator or spectrometer to a second end of the ion mobility separator or spectrometer; and applying one or more transient DC voltages to the one or more spiral electrodes in order to urge ions towards the first end of the ion mobility separator or spectrometer.

According to an aspect of the present invention there is provided a method of separating ions comprising:

supplying ions to a radio frequency ion guide;

driving ions in one direction such that ions with different characteristics separate; and driving ions in the opposite direction in a manner effectively independent of the ions characteristics, such that ions with different characteristics do not effectively separate.

According to the preferred embodiment the driving forces are electrostatic.

According to the preferred embodiment components of the two opposing driving forces are preferably substantially orthogonal to each other.

According to the preferred embodiment at least one of the driving forces is preferably time and or position varying.

According to the preferred embodiment the separation is preferably related to ion mobility in a buffer gas.

According to another embodiment the separation may be related to the mass to charge ratio of the ions.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; and (xx) a Glow Discharge ("GD") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wein filter; and/or (k) a device or ion gate for pulsing ions; and/or (l) a device for converting a substantially continuous ion beam into a pulsed ion beam.

The mass spectrometer may further comprise either:

(i) a C-trap and an Orbitrap® mass analyser comprising an outer barrel-like electrode and a coaxial inner spindle-like electrode, wherein in a first mode of operation ions are transmitted to the C-trap and are then injected into the Orbitrap® mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap® mass analyser; and/or (ii) a stacked ring ion guide comprising one or more electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The ion mobility spectrometer according to the preferred embodiment may comprise one or more electrodes each having an aperture through which ions are transmitted in use. One or more transient DC voltages or potentials or one or more DC voltage or potential waveforms are preferably applied to the electrodes comprising the ion mobility spectrometer in order to urge ions along the length of the ion mobility spectrometer.

According to the preferred embodiment the one or more transient DC voltages or potentials or the one or more DC voltage or potential waveforms create: (i) a potential hill or barrier; (ii) a potential well; (iii) multiple potential hills or barriers; (iv) multiple potential wells; (v) a combination of a potential hill or barrier and a potential well; or (vi) a combination of multiple potential hills or barriers and multiple potential wells.

The one or more transient DC voltage or potential waveforms preferably comprise a repeating waveform or square wave.

An RF voltage is preferably applied to the electrodes of the ion mobility spectrometer and preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; (xi) 500-550 V peak to peak; (xxii) 550-600 V peak to peak; (xxiii) 600-650 V peak to peak; (xxiv) 650-700 V peak to peak; (xxv) 700-750 V peak to peak; (xxvi) 750-800 V peak to peak; (xxvii) 800-850 V peak to peak; (xxviii) 850-900 V peak to peak; (xxix) 900-950 V peak to peak; (xxx) 950-1000 V peak to peak; and (xxxi) >1000 V peak to peak.

The RF voltage preferably have a frequency selected from the group consisting of: (i) <100 kHz; (ii) 100-200 kHz; (iii)

200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The ion mobility spectrometer is preferably maintained at a pressure selected from the group comprising: (i) >0.001 mbar; (ii) >0.01 mbar; (iii) >0.1 mbar; (iv) >1 mbar; (v) >10 mbar; (vi) >100 mbar; (vii) 0.001-0.01 mbar; (viii) 0.01-0.1 mbar; (ix) 0.1-1 mbar; (x) 1-10 mbar; and (xi) 10-100 mbar,

BRIEF DESCRIPTION OF THE DRAWINGS

Various embodiments of the present invention will now be described, by way of example only, and with reference to the accompanying drawings in which:

FIG. 1 shows an ion mobility separator according to a preferred embodiment;

FIG. 14A shows a plan view and FIG. 14B shows a side view of another embodiment of the invention;

FIG. 15A shows a plan view and FIG. 158 shows an end view of another embodiment of the invention;

FIG. 16 shows a plan view of another embodiment of the invention; and

FIG. 17 shows a plan view of another embodiment of the invention.

DETAILED DESCRIPTION OF THE PREFERRED EMBODIMENTS

Figure 2A:
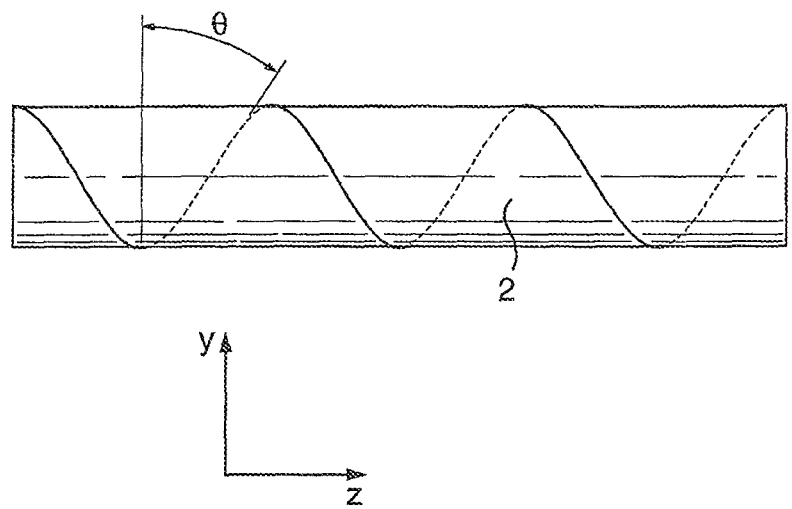
FIG. 2A shows a spiral of conductive material attached to the outside of an inner cylinder of the ion mobility separator and FIG. 2B shows a spiral of conductive material attached to the inside of an inner cylinder of the ion mobility separator.

A preferred embodiment of the present invention will now be described with reference to FIG. 1. It should, however, be understood that the present invention is not restricted to an ion mobility spectrometer and numerous alternative geometries to the annular geometry shown in FIG. 1 are intended to fall within the scope of the present invention.

According to an embodiment of the present invention an ion mobility separator may be provided comprising two concentric cylinders as shown in FIG. 1. The cylinders comprise an outer cylinder 1 and an inner cylinder 2 defining an annular volume through which ions pass in use. The concentric cylinders are preferably made of a non conductive material. The ion mobility separator preferably has an entrance end 3 through which ions enter the ion mobility separator and an exit end 4 through which ions exit the ion mobility separator.

The annular volume between the two concentric cylinders 1,2 is preferably supplied with a buffer gas or drift gas such as helium or nitrogen. For example, the pressure of drift gas in the annular volume may be set to between 0.5 torr to 5 torr.

Figure 2B:
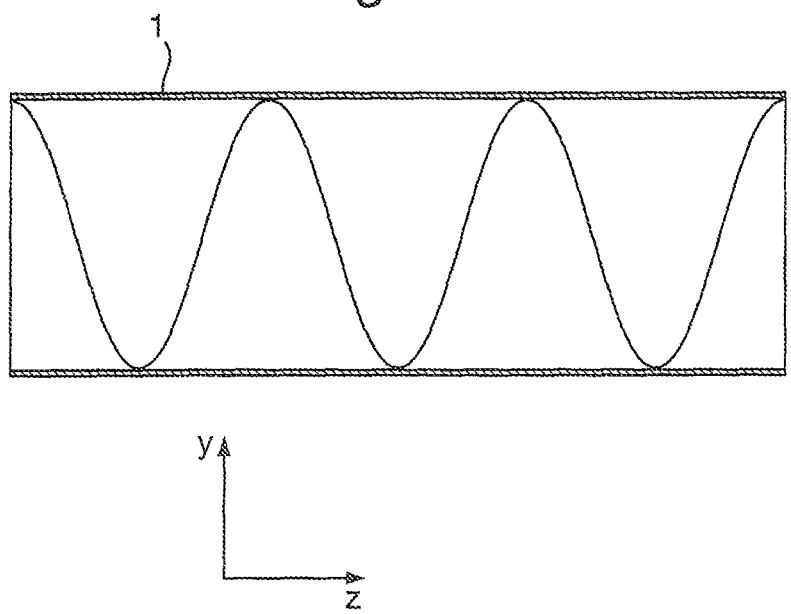

According to a specific embodiment a spiral of conductive material may be attached to the outside of the inner cylinder 2 as shown in FIG. 2A. A spiral of conductive material may also be attached to the inner surface of the outer cylinder 1 as shown in FIG. 2B. The inner and outer spirals are preferably arranged such that the inner spiral follows the path of the outer spiral over the length of the device. As an example, if the angle θ of the conductive strip with respect to the y axis as shown in FIG. 2A is 20° and the diameter of the inner cylinder 2 is 20 mm, then the strip will make one complete revolution of the cylinder every 22.87 mm. For a 100 mm cylinder length the wire would make 4.37 complete revolutions of the cylinder. The overall length of the conductive track would be approximately 292 mm. If the diameter of the outer cylinder 1 were 30 mm then an annulus of 5 mm radial width will be formed between the outer cylinder 1 and the inner cylinder 2.

Figure 3:
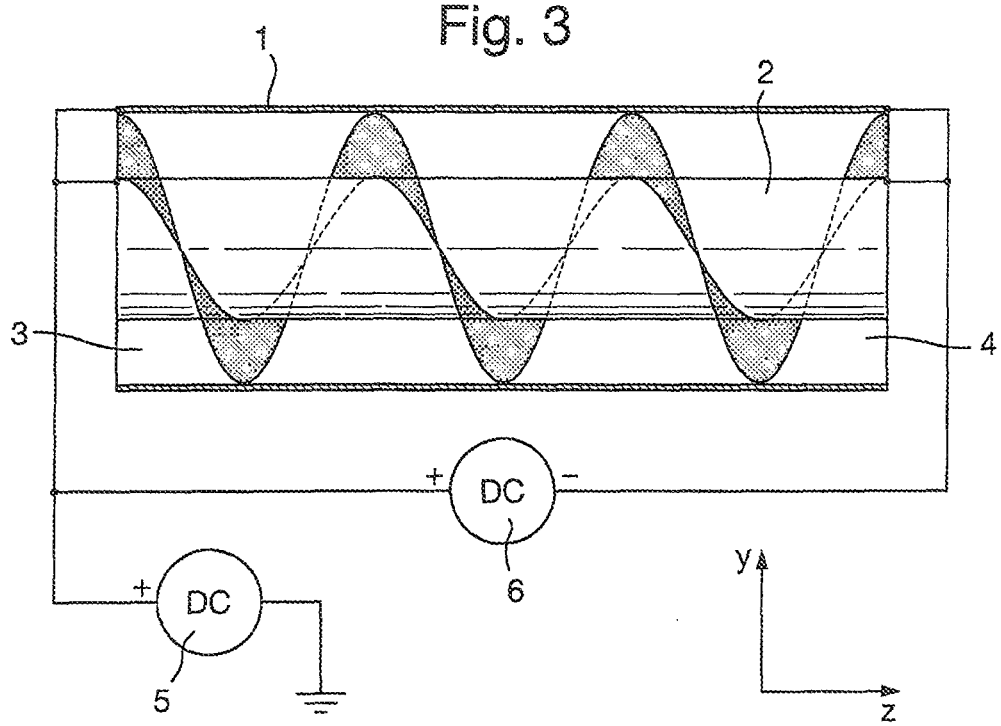
FIG. 3 shows a single helical DC barrier formed within the device.

FIG. 3 shows the inner cylinder 2 and the outer cylinder 1 each in the z,y direction with complimentary spiral conductive strips. A first DC power supply 5 is provided to allow the potential of the conductive strip to be raised thereby producing a helical DC potential barrier along the annular volume. The resulting DC potential barrier is indicated by the shaded area between the inner and outer spiral tracks in FIG. 3.

The conductive strip may be resistive and such that the total resistance of the strip may be of in the order of 50-500Ω. This allows a potential gradient to be applied from one end of the conductive strip to the other using a second DC supply 6.

Figure 4:
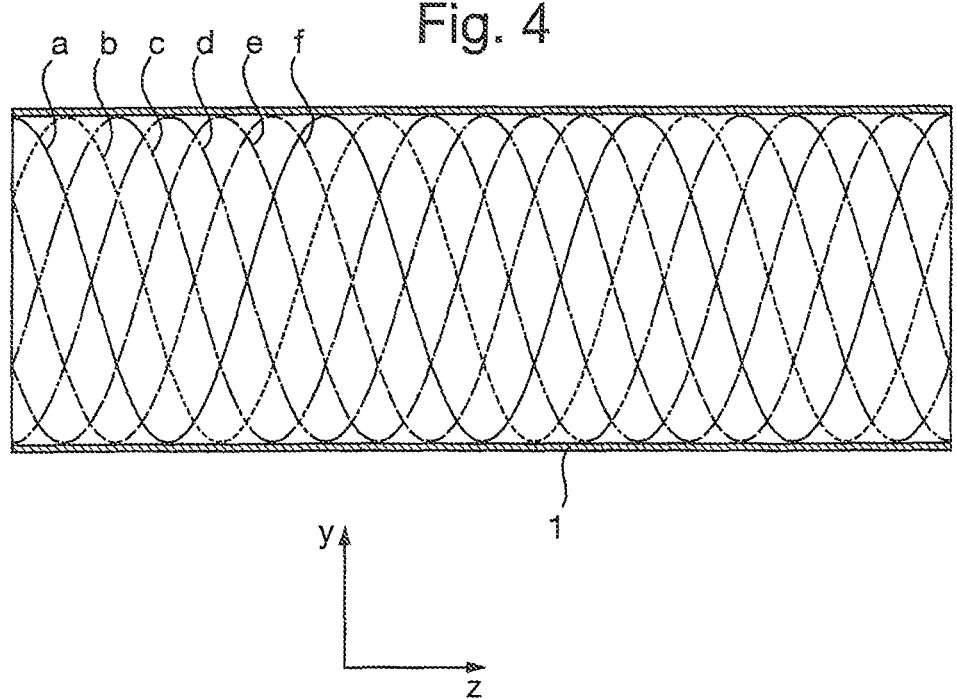
FIG. 4 shows detail of the preferred embodiment.

FIG. 4 shows an embodiment wherein the outer cylinder 1 comprises six equally spaced conductive resistive strips a,b, c,d,e,f forming six spirals. Using the example of a 20 mm diameter inner cylinder and a 20 degree angle θ, for a strip width of 0.5 mm and gap between strips of 1 mm a total of 15 strips may be applied to the inner cylinder 2.

In operation the second DC supply 6 may be arranged to apply a DC potential to all six conductive strips effectively producing a DC field which acts to urge ions from the entrance end 3 of the ion mobility separator to exit end 4 of the ion mobility separator. However, the first DC supply 5 is preferably only applied to one of the spiral conductive strips at any specific time.

The same potentials are preferably applied to the complimentary conductive strips on the inner cylinder 2.

In the preferred embodiment ions may be confined radially in the annular volume 3 by application of an AC voltage oscillating at RF frequency to the conductive strips. The RF voltage between adjacent strips is preferably 180° out of phase.

Figure 5:
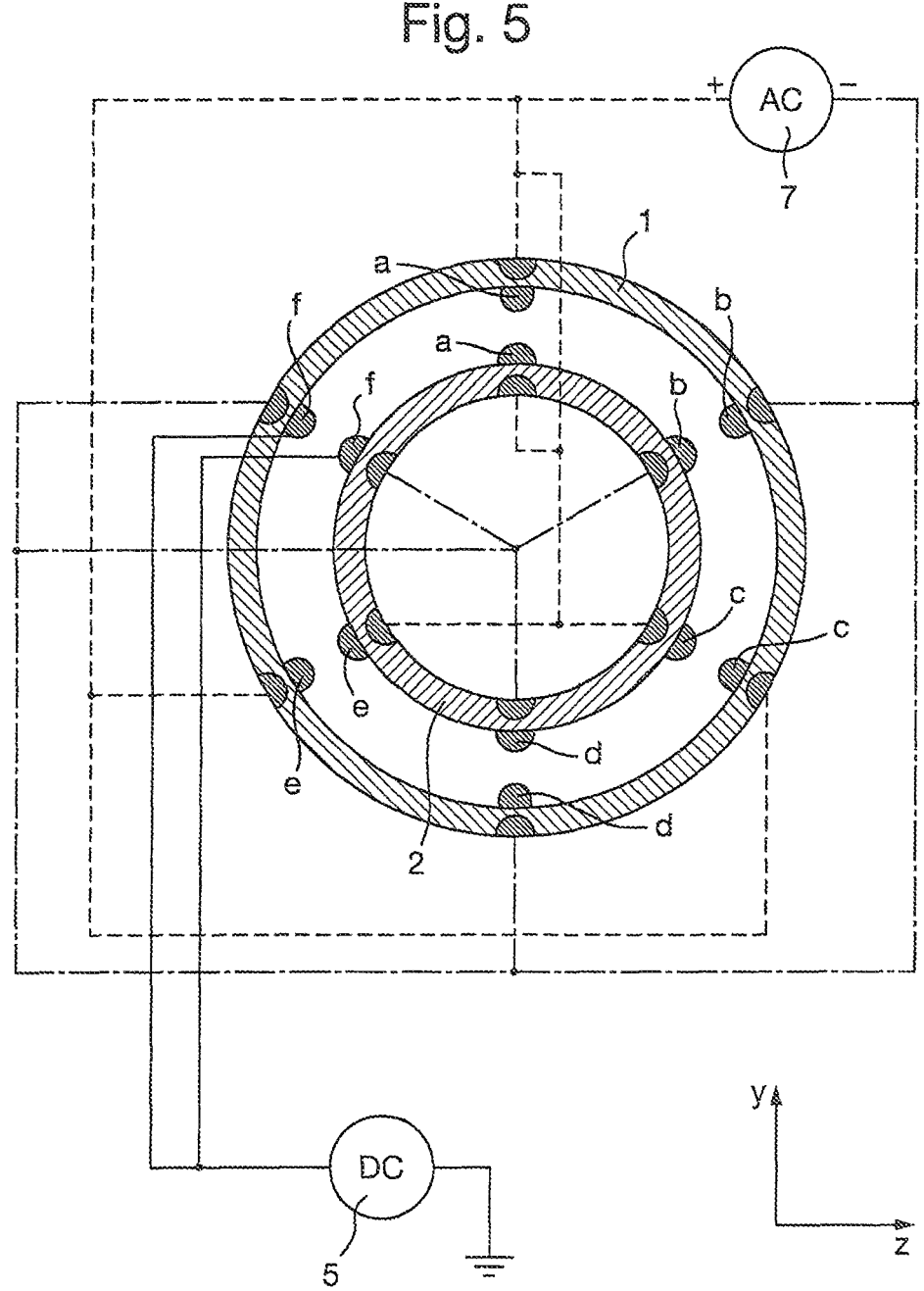
FIG. 5 shows the preferred embodiment in the (x, y) plane.

FIG. 5 shows a view of the outer cylinder 1 and inner cylinder 2 in the x,y direction illustrating how the confining RF and the spiral DC barrier may be applied to the inner cylinder 2 and outer cylinder 1.

Both the inner cylinder 2 and outer cylinder 1 may be made from made from a dielectric material with conductive strips on the inside and outside of each cylinder. For example a flexible PCB construction may be used.

DC electrodes a,b,c,d,e,f are shown in FIG. 5 on the outside of the inner cylinder 2 and on the inside of the outer cylinder 1.

Also shown in FIG. 5 are auxiliary conductive strips running parallel to electrodes a,b,c,d,e,f but on the opposite side of the cylinders of dielectric material. The auxiliary strips preferably follow the same spirals as described for each of the electrodes a,b,c,d,e,f down the length of the device. The auxiliary electrodes may be supplied with AC potential oscillating at RF frequency with adjacent electrodes preferably supplied with opposite phases of RF. The AC potential preferably capacitively couples onto to the DC electrodes via the dielectric material resulting in a radial RF confining field within the annular volume. The AC voltage may, for example, have an amplitude of 400 V pk to pk and a frequency of 1 MHz.

In operation ions are preferably pulsed into the ion mobility separator at a time T1 via the entrance 3 of the ion mobility separator. At time T1 the potential applied to strip f as shown in FIGS. 4 and 5 is preferably raised above the potential of the other five spiral strips thereby effectively forming a barrier through which ions may not pass. Ions are preferably arranged to enter the ion mobility separator in a region away from conductive strip f so that their initial transit into the ion mobility separator is not impeded.

The potential gradient applied across each strip by the first DC voltage supply 5 preferably urges ions to progress down the ion mobility separator in a spiral path following the path DC barrier produced by the potential applied to strip f.

The component of the field which results in separation of the ions is preferably orthogonal to the DC barrier.

Ions passing through the buffer gas are preferably driven in a spiral path by the spiral DC gradient and will separate according to their ion mobility.

As the ions travel down the device at a subsequent time T2, where T2>T1, the DC voltage applied to strip f is preferably removed and a DC voltage is preferably applied only to strip e as shown in FIG. 4. Therefore, at time T2 DC the potential of strip e is preferably raised with respect to the other conductive strips. At a subsequent time T3, where T3>T2, the DC potential barrier is preferably switched to conductive strip d only. At a subsequent time T4 the DC potential is applied only to strip c. At a subsequent time T5 the DC is preferably applied only to strip b. At a subsequent time T6 the DC is preferably applied only to strip a. Finally, at a subsequent time T7, wherein T7>T6>T5>T4>T3>T2>T1, the DC is preferably applied only to strip f. This pattern is preferably repeated throughout the analysis.

Applying the DC voltage to strips a,b,c,d,e,f in this way creates a travelling DC helix or a rotating DC helix acting to oppose the motion of ions through the device as they are urged through the drift gas by the DC potential gradient applied to each conductive strip. Ions are preferably urged back towards the entrance of the device by the DC helical travelling wave but, at the same time, the ions slip down the inclined helical wave front as they are moved towards the exit of the device by the applied DC gradient.

By adjusting the speed of the travelling helical wave or the strength of the DC field the residence time of ions within the device can be extended. Ions experience a DC field acting towards the exit of the device for a longer period of time than would be expected if no helical travelling wave were present. This longer residence time is equivalent to the ions travelling through a proportionately longer ion mobility separation device and hence the ion mobility separation power is increased compared to a conventional ion mobility separation device of a comparable physical length.

Figure 6:
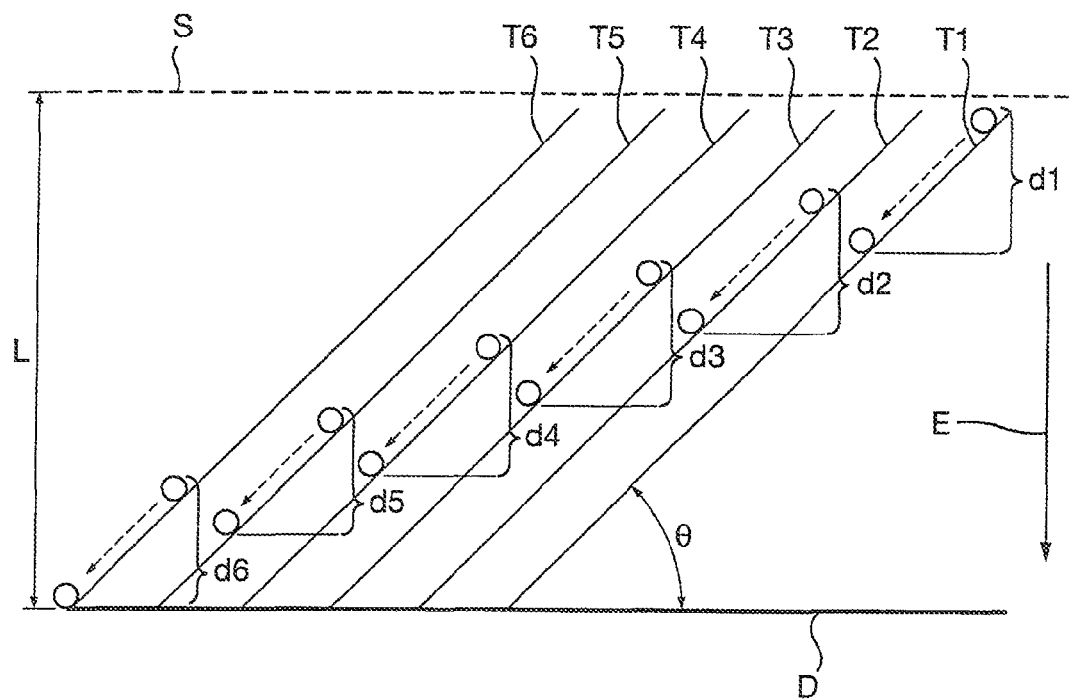
FIG. 6 illustrates the principle involved in the invention.

To aid conceptualisation of the principle of operation of the device described, a simple model may be imagined wherein the travelling helical DC barrier is stretched out to form a linear barrier existing on a flat plane. FIG. 6 represents a single ionic species within such a model. The diagonal line labelled T1 represents a DC barrier existing at time T1 over which ions cannot pass. In this diagram the barrier traverses a flat plane with the height of the barrier extending vertically towards the viewer. This barrier is inclined with respect to the plane of the ion detector or exit of the device D by the angle θ. The length L defines the length of the device from the entrance plane S to the exit plane D. An electric field E exists over the length L of the device urging ions from the entrance to the exit plane. In this model ions exist in an elevated pressure of buffer gas such that ion motion is dominated by the ion mobility K.

At time T1 ions are preferably urged in a direction along the inclined edge of the DC barrier by the component of the DC force E resolved in this direction. If the DC barrier at T1 is static then ions will eventually reach the exit of the device D after travelling a distance L in field E. The time for the ions to travel from the entrance to the exit (DTs) will depend on the mobility of the ion and will be given by:

$$DTs = \frac{L}{KE} \quad (2)$$

However, in FIG. 6 the ion is allowed to travel distance d1 through the device until time T2. In this example d1=L/4.

At time T2 the DC barrier is preferably moved upwards towards the entrance of the device and now exists at the position labelled T2. The ion preferably moves on the front of this barrier in a direction normal to the barrier. Ions of all mobility values are preferably moved by substantially the same amount. As shown, the ion has been moved towards the entrance of the device and again starts to move down the barrier which is now shown in position T2. The ion is preferably allowed to travel a distance d2, where d2=d1, under the influence of electric field E until time T3. At time T3 the barrier has again been moved and the ion has been pushed back towards the entrance. The ion is again allowed to drift a distance d3, where d1=d2=d3, until time T4 where the barrier is again moved. The ion is then allowed to travel distance d4, where d1=d2=d3=d4, before the barrier is moved again at time T5. The ion is then allowed to travel distance d5, where d1=d2=d3=d4=d5, before the barrier is moved again at time T6. Finally, the ion is allowed to move a distance d6, where d1=d2=d3=d4=d5=d6 at which point the ion exits the device.

The overall distance that the ion has travelled in the field E (Lt) is:

$$Lt = 6 \times d1 \quad (3)$$

This can be compared to the distance over which the ion would have travelled in the same field if the inclined barrier had not been moved L:

$$L = 4 \times d1 \quad (4)$$

Thus the absolute length of the mobility separation device L can be extended to a longer virtual length Lt. The amount that the drift length is extended is a function of the ions mobility.

To investigate the performance of this technique in terms of mobility separating power, a model similar to the theoretical model described in FIG. 6 was constructed using SIMION® ion optic simulation software.

The parameters used in this model were length of drift region L is 100 mm, height of DC barrier is 100V, angle of DC barrier wrt exit plane θ=20°, pressure of nitrogen (hard sphere model) P is 0.5 Torr, speed of barrier normal to wave front is 40 m/s and driving field E is 4 V/mm.

The trajectories of four ions were modelled. All ions were singly charged with mass to charge ratio 500 but with differing mobility values. Ion #1 had K=0.173 $M^2V^{-1} s^{-1}$ and cross section of 200 Å$^2$; Ion #2 had K=0.139 $M^2V^{-1} s^{-1}$ and cross section of 250 Å²; Ion #3 had K 0.126 M²V⁻¹ s⁻¹ and cross section of 275 Å²; and ion #4 had K=0.115 M²V⁻¹ s⁻¹ and cross section of 300 Å².

Groups of 1000 ions of each mobility value were modelled and the mean drift time and the standard deviation in drift time for each species was recorded.

Figure 7:
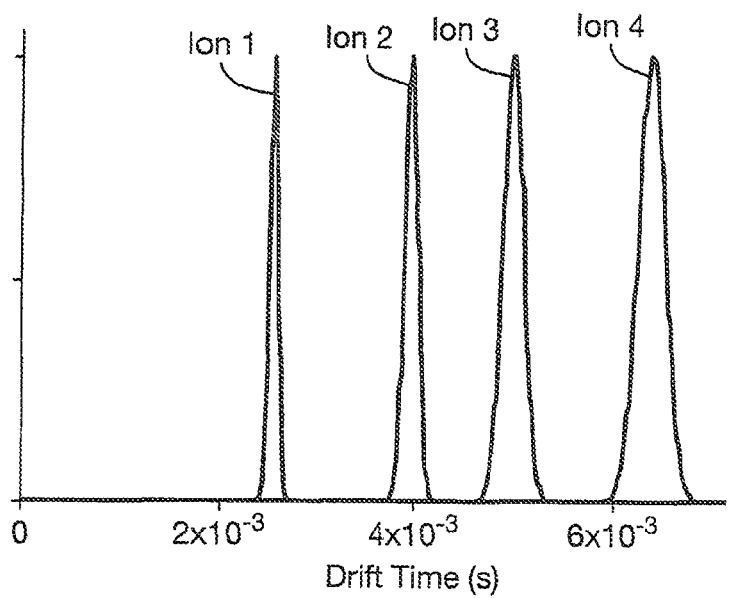
FIG. 7 shows the results of a SIMION simulation.

FIG. 7 shows the results from SIMION® for this model. Peaks are represented as Gaussian peaks with mean and standard deviations measured from the output of the simulation.

Figure 8:
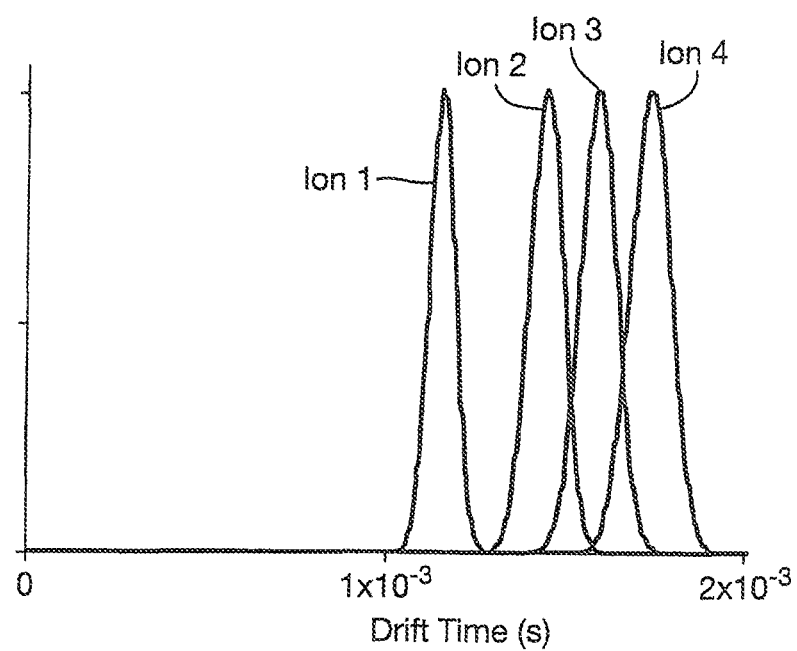
FIG. 8 shows a comparison with the prior art.

FIG. 8 shows the theoretical IMS spectrum of the same group of ions separated in a standard IMS drift tube at the same pressure, length and field as the example modelled in FIG. 7.

There is clearly a marked improvement in IMS separation power using the technique according to the preferred embodiment. This is accompanied as expected by an increase in the drift time for all the species.

It can also be seen, by comparison of FIGS. 7 and 8, that the difference in drift time for the ions of high mobility is less than the difference for the low mobility ions. This demonstrates that the increase in the drift time for these ions is dependent on the mobility.

Because the drift time is not linearly dependent on the mobility of the ions, the mobility resolution R can no longer be calculated directly from the expression:

$$R = \frac{DT}{\Delta Dt} = \frac{K}{\Delta K} \quad (5)$$

To produce an expression for the resolution of the device an analytical expression is required describing the motion of the ions within the travelling helical wave.

Figure 9:
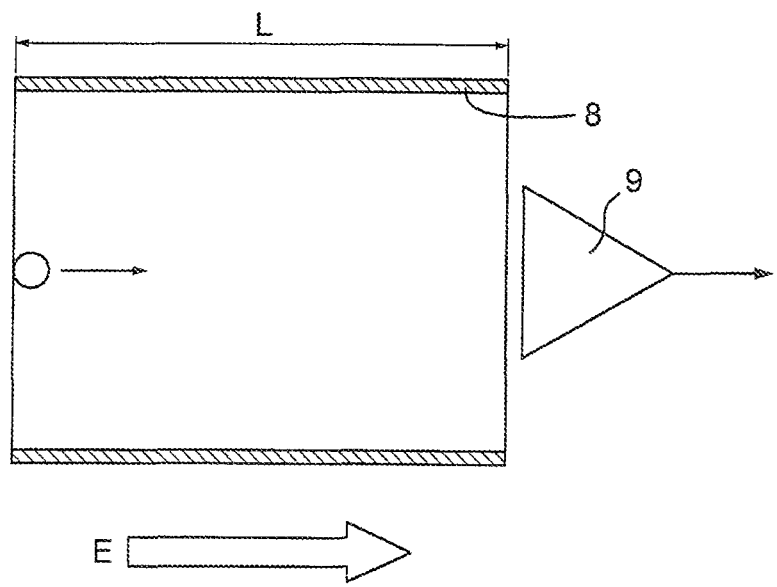
FIG. 9 shows a simplified model of ions motion in the device disclosed.

FIG. 9 shows a further simplification illustrating the principal of the preferred embodiment. A drift tube 8 of length L is supplied with a field E urging ions along the tube 8 through a buffer gas with velocity V wherein:

$$V = K \cdot E \quad (6)$$

A detector 9 is placed initially at the end of the drift tube 8 and moves away from the exit of the drift tube 8 with a constant velocity Vd effectively increasing the total length of the tube $L_{tot}$ as the ions drift. The field E is assumed to be constant throughout the ions journey to the detector 9.

The time $t_{tot}$ at which an ion reaches the receding detector 9 is given by:

$$t_{tot} = \frac{L}{KE - V_d} \quad (7)$$

The extent to which a packet of ions introduced into the drift cell spreads with time is governed by diffusion within the buffer gas.

The standard deviation in the width if the ion packet with time σL is given by:

$$\sigma L = \sqrt{\frac{2kTKt}{q}} \quad (8)$$

wherein k is Boltzmann constant, T is the temperature in Kelvin, t is the drift time and q is the charge on the ion.

The standard deviation in terms of time at for the system may found by division of Eqn. 8 by the relative velocity of the ion given by Eqn. 7:

$$\sigma t = \sqrt{\frac{2kTKt}{q}} \cdot \frac{t}{L} \quad (9)$$

The FWHM of the mobility peak in time Δt is:

$$\Delta t = 2\sqrt{2\ln 2} \cdot \sigma t \quad (10)$$

To compare the results from the SIMION® model described an additional factor must be applied to represent the ion arriving at the detector 9 at a non normal angle θ. This has the effect of reducing the observed FWHM peak width by a factor F, wherein F=sin (θ).

Figure 10:
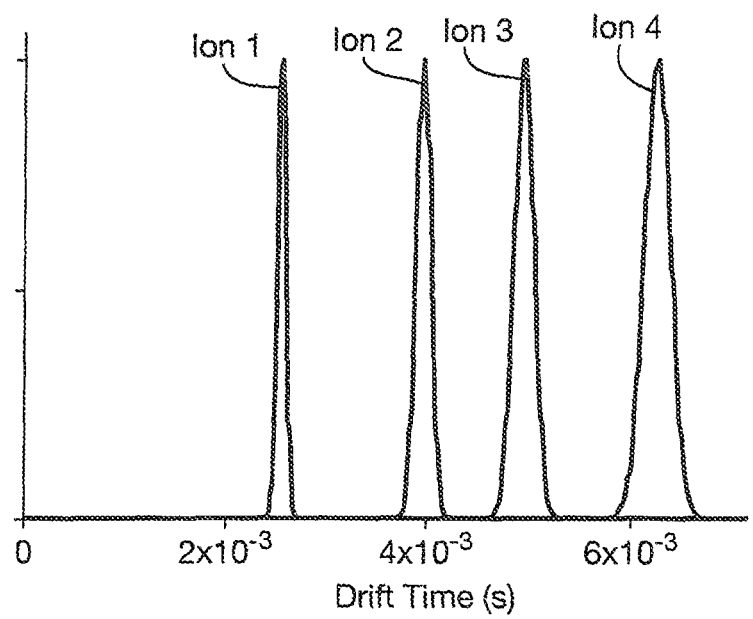
FIG. 10 shows the results of an analytical model describing the ion separation within the device.

FIG. 10 shows the results from this approach for the same ions ion #1, Ion #2, Ion #3 and Ion #4 as shown in FIGS. 7 and 8.

In this model the drift region L was modelled as 100 mm, the velocity $V_d$ of the detector was 29 m/s and the driving field E was 4 V/mm.

There is very good agreement with the results from the SIMION® simulation shown in FIG. 7 suggesting that this is a very good analytical approximation.

To derive an expression for mobility resolution using this model, Eqn. 2 may be re-written as:

$$R = \frac{K}{\Delta K} = \left| \frac{K}{\Delta t} \cdot \frac{dt_{tot}}{dK} \right| \quad (12)$$

Substituting Eqns. 7 and 8 into Eqn. 9 and evaluating yields an expression for the mobility resolution R of the device for a given detector velocity. The detector velocity is analogous to the speed of rotation of the helical DC barrier in the preferred embodiment:

$$R = \frac{E\sqrt{K \cdot L \cdot q}}{\sqrt{16\ln(2)kT(KE - V_d)} \cdot \sin(\theta)} \quad (13)$$

Figure 11:
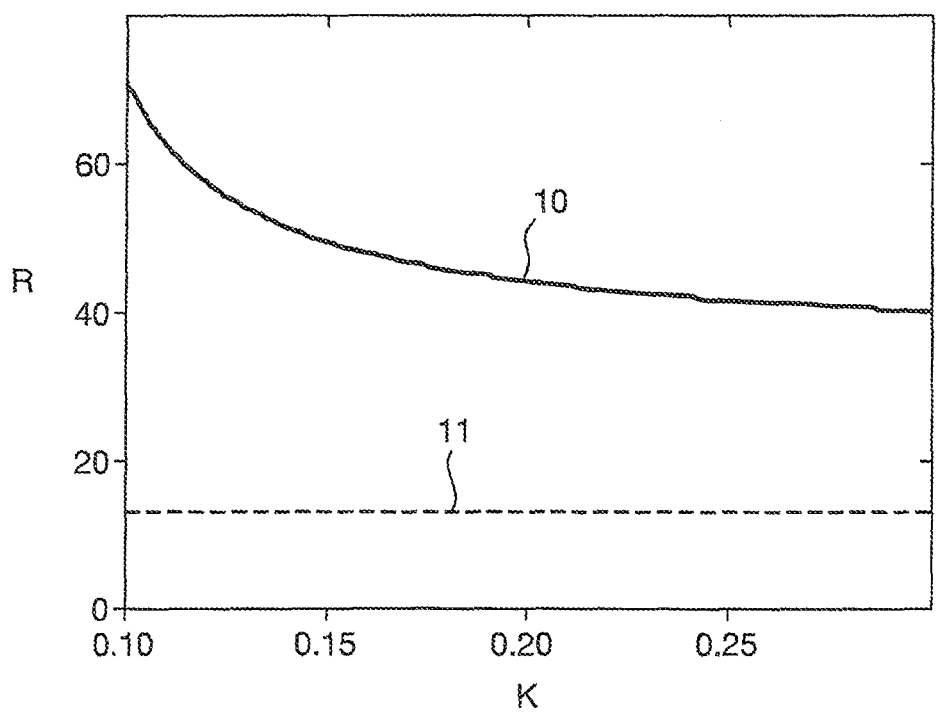
FIG. 11 shows a graph of resolution versus mobility value.

FIG. 11 shows a plot of mobility resolution R versus K value. The solid line 10 represents the theoretical resolution from the device under the conditions used in the SIMION® simulation and analytical model described.

The dashed line 11 shows the resolution obtained from a standard DC drift tube of the same length L operating at the same pressure and field E. A mobility resolution of 13 was calculated for the standard drift tube. Increases in resolution of between 3 and 5 are achieved over this range of mobility according to the preferred embodiment. To achieve these resolutions at the same pressure and field using a standard drift tube a drift tube length of between 0.9-2.5 m would be required which is impractical. The mobility resolution is dependent of the mobility of the ion as the total effective distance the ions travel in the applied field depends on the ions mobility.

In the embodiment described, ions are driven towards the exit of the device by the DC field acting along the helical DC barrier and are moved back towards the exit of the device by sweeping or rotating the DC barrier. Ions eventually exit in the direction in which they are urged by the DC field and may be detected. However, improved IMS separation may also be achieved by driving ions such that they exit in the opposite direction i.e. in the direction in which they are urged by the travelling or rotating helical DC barrier.

Figure 12:
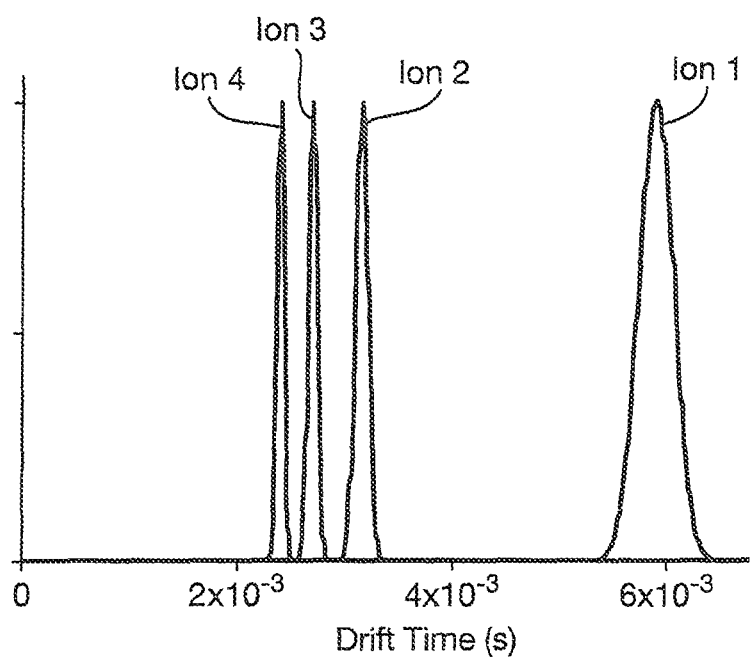
FIG. 12 shows the results of an analytical model describing the ion separation within the device.

FIG. 12 shows the results of a SIMION® ion optical simulation for the model as described for FIG. 7. However, the speed of the travelling barrier was increased from 40 m/s to 94 m/s. Ion arrival times are recorded as the ions exit the device in the direction of the wave front.

The order in which the four species modelled elute from the device is reversed with ions having relatively low ion mobility exiting the device before ions with higher mobility.

Figure 13:
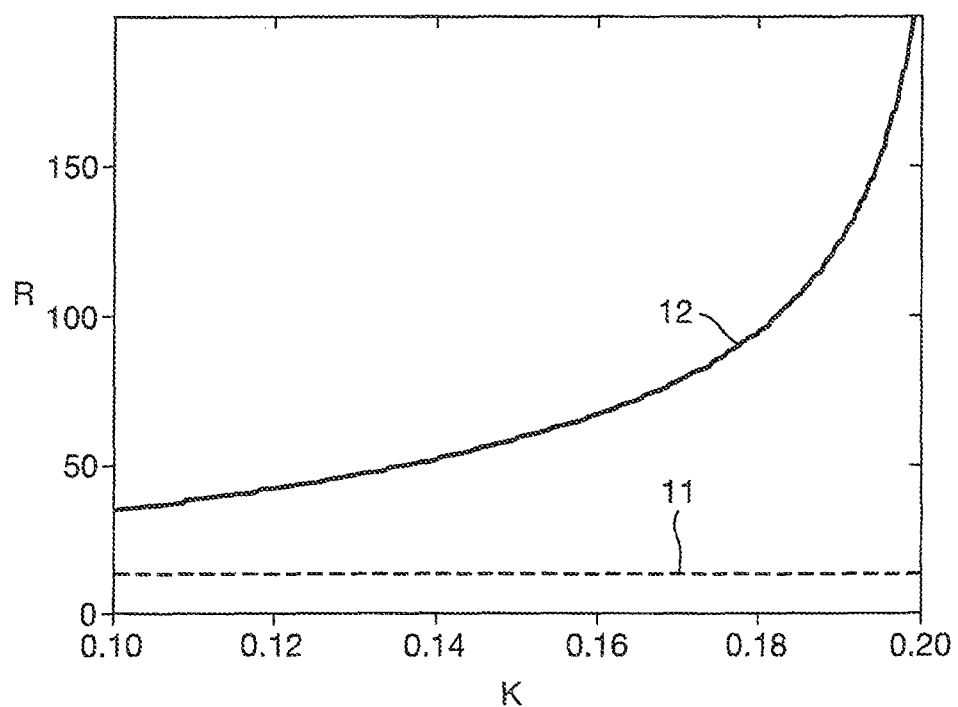
FIG. 13 shows a graph of resolution versus mobility value.

FIG. 13 shows a plot of mobility resolution R versus mobility K calculated using a very similar analytical approach as described for FIG. 10. However, in this model the detector is arranged at the entrance to the device and 'catches up' with the ions as they separate in the DC field. The resolution for a standard drift tube under the same conditions is shown as a dotted line 11. The resolution for this standard drift tube is 13.

It should be noted that that during IMS separation the amplitude of the DC field may be ramped or stepped over a range of values and/or the velocity of the travelling spiral DC barrier may be ramped or stepped over a range of values. In this mode of operation the resolving power of the device may be maximised for specific mobility ranges.

In another mode of operation an additional DC or RF barrier may be arranged at one end of the device (or at some point along the length of the device) such that once ions have entered the device they cannot exit or travel past this point. By adjusting the magnitude of the DC field and the speed of the opposing travelling DC helix, all ions may be driven to the end of the device and can effectively be trapped at a specific location within the device. Ions may be trapped by a combination of the exit barrier and the DC travelling spiral or by the exit barrier and the DC field acting along the length of the DC spiral.

Once ions are trapped they can be scanned out by ramping or stepping the amplitude of the DC field or by ramping or stepping the velocity of the travelling helical DC barrier or by a combination of both. In this mode of operation the resolving power of the device may be maximised for a wide range of mobilities.

By varying the driving forces within the device it is possible to arrange ions with different mobility ranges to exit via different ends of the device simultaneously if desired.

In the preferred embodiment ions enter the device at one end of the annular volume, however, ions may be arranged to enter the annular volume at any point along the length of the device via a separate ion entrance through the outer cylinder.

The device may also be operated as an ion guide without any IMS separation according to another mode of operation. In this mode of operation the DC field acting to urge ions along the DC spiral barrier may be effectively set to zero and the travelling DC spiral may be used to drive ions through the device. The travelling or rotating DC spiral may be used to transmit a continuous, discontinuous or pulsed ion beam.

The device will operate as an RF ion guide over a wide range of buffer gas pressure. The transit time of ions through the device may be precisely controlled by adjusting the speed of the travelling DC spiral as described.

At an elevated buffer gas pressure the travelling spiral DC barrier can transport a continuous beam of ions or a discontinuous beam of ions with no effective mobility separation. This is not possible using a static axial DC driving force.

At an elevated buffer gas pressure the travelling spiral DC barrier can transport a continuous beam of ions or a discontinuous beam of ions with no effective mobility separation and no partitioning of the ion beam. This is not generally possible using a conventional DC travelling wave gas cell.

When used with a continuous ion beam the device may be used as a high or low mobility cut off filter. For example. the speed of the travelling DC helical barrier opposing the DC field may be adjusted so that only ions having an ion mobility above a certain mobility value will exit the device. Ions of lower mobility will not be driven towards the exit of the device or will be driven back towards the exit.

Although the preferred embodiment has a cylindrical geometry other embodiments with planar and other geometries are also intended to fall within the scope of the present invention.

FIG. 14A shows a plan view of another embodiment with a planar geometry shown in the x,y plane. This embodiment is similar to FIG. 6. Horizontal planar electrodes are segmented into a plurality of electrode segments. Ions enter the device at entrance 3 and are driven along a horizontal diagonal DC barrier 14 by an electric field E. The position of the diagonal DC barrier is swept with time in the direction shown by the arrow 15. Ions of different mobility will exit at different points along the length of the device W.

FIG. 14B shows a side view of the device in the x,z plane. Ions are preferably confined vertically within the array of electrodes by a pseudo-potential well due to an RF voltage being applied to the upper and lower arrays of segmented electrodes.

Although this is not as compact a design as the preferred embodiment, the mobility resolution which can be achieved for a given length L is significantly higher than can be achieved with a standard drift tube of length L with a field E.

Figure 15A:
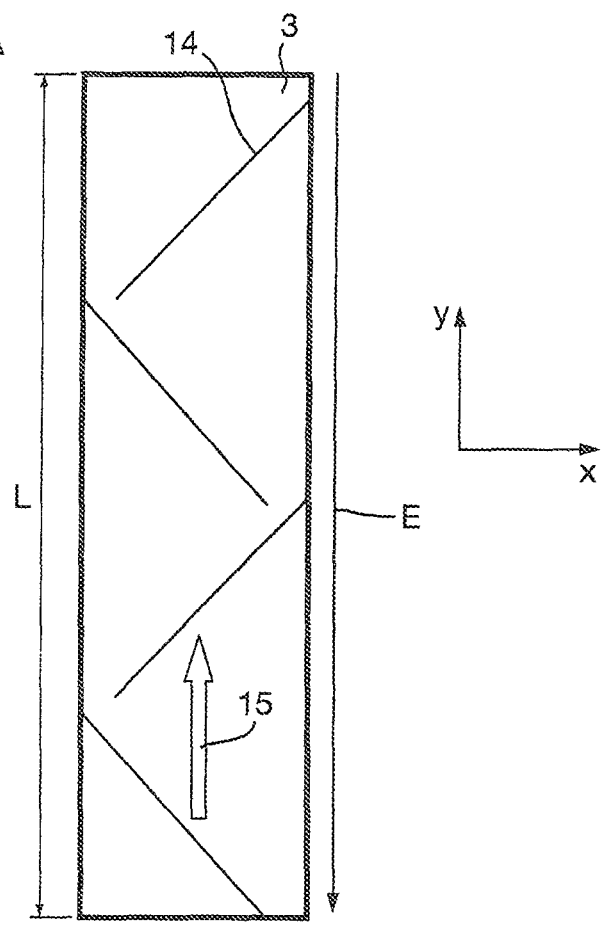

Another planar embodiment is shown in FIG. 15A in the x,y direction. FIG. 15A shows a plan view. Ions enter at entrance 3 and are driven along a diagonal DC barrier 14 by an electric field E. The DC barrier is discontinuous over the length of the device L allowing ions to reverse their direction in the x axis as they travel through the device. The positions of the multiple DC barriers are swept with time in the direction shown by the arrow 15.

Figure 15B:
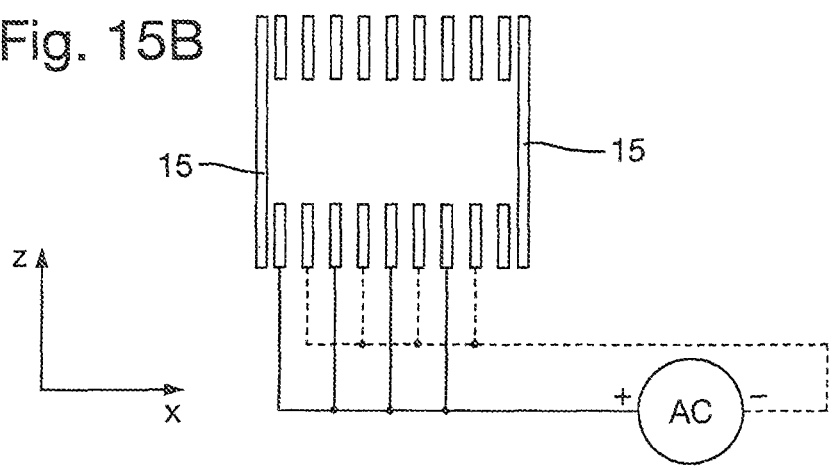

FIG. 15B shows an end view of the device in the x,z direction. Ions are contained in the z (vertical) direction by supplying the upper and lower arrays of segmented electrodes supplied with RF voltage which results in a pseudo-potential well. Ions are contained in the x direction by electrodes 15 supplied with DC voltage.

Various different methods of containing ions in the z and x directions for the embodiments shown in FIGS. 14 and 15 are contemplated.

FIG. 16 shows a plan view of a representation of another embodiment with a planar geometry in the x,y. In this case ions enter at entrance 3 and are driven along a planar spiral DC barrier by an electric field E which acts radially towards the centre of the spiral. The position of the spiral DC barrier is moved with time such that the spiral rotates around its central point in the direction indicated by the arrow 16. The spiral shown in FIG. 16 represents the location of a DC potential barrier.

Ions eventually exit the device at the central point 17. In this embodiment ions may be injected at the centre of the spiral and driven towards the outside of the spiral by increasing the speed of rotation of the spiral DC barrier or by decreasing the field E sufficiently.

It should be noted that the direction of both the radial field and the direction of rotation of the spiral may be reversed without changing the principle of operation.

As for the embodiments in FIGS. 14 and 15 ions may be contained in the x,z (vertical) plane using an array of RF electrodes.

In the embodiments described in FIGS. 14, 15 and 16 the total time that ions spend in the electric field and hence the resolution of the device may be adjusted, in a mobility dependant way, by changing the speed of movement of the DC barrier or by ramping the electrostatic field.

FIG. 17 shows another embodiment similar to that shown in FIG. 16. In this embodiment the device acts within ion trapping properties. Ions enter the device at entrance 3 and are driven in the direction shown by arrow 18 along a partial spiral barrier by a combination of the electrostatic field E acting radially towards the centre of the device and the force applied to the ions by rotation of a DC potential spiral barrier in the direction shown by arrow 16. In this case the speed of rotation of the DC potential spiral barrier is chosen such that ions are driven towards the outside of the spiral. When ions reach the end of the spiral 19 they are driven by the electric field E between one end of the spiral 19 and a point near the other end of the spiral 20. They then continue to cover the same path round the spiral back to point 19. The ions are effectively trapped on the edge of the spiral barrier and separate as they proceed to revolve around the central point 17. As the ions do not take a unique path ions with low mobility will eventually catch up with the ions of higher mobility which travel around the device with a lower relative velocity. Ions may be ejected from the device, for example, by removing a portion of the barrier at point 20 and by allowing ions to fall to the centre or by removing the field E acting radially towards the centre of the device. In the latter case ions will exit in a direction indicated by the arrow 21. According to this embodiment ions may be arranged to exit the device in reverse order of ion mobility.

Various modifications to the embodiments shown and described above are contemplated.

For example, modifications may be made to the way in which the time and position varying DC barrier is applied. For example, rather than applying the potential in a series of discreet steps with potentials suddenly appearing and disappearing on different elements of the device, the amplitude of the DC potential may be applied and then removed using a smooth continuous function. This allows for a smoother transition between the travelling waves experienced by the ions.

In the preferred embodiment described above the potential forming the travelling DC barrier is shown and described as being applied to only one conductive strip at a time. However, it may also be advantageous to apply the potential to groups of adjacent conductive strips. Other embodiments are contemplated which affect the magnitude and the shape of the travelling wave.

The confining RF voltage may be applied in other ways than described in the preferred embodiment. For example, the RF confining potential may be applied between the complimentary spirals on the inner and outer cylinder such that the conductive strips on the inner cylinder are supplied with RF potential 180 degrees out of phase with the strips on the outer cylinder. All strips on the inner cylinder may be arranged to be at the same phase and all strips on the outer cylinder may be arranged to be at the same phase.

Alternatively, the RF confining potential may be applied such that spirals on the inner cylinder have opposite phases to the complimentary spirals on the outer cylinder. However, adjacent spirals on the inner and the outer may have opposite phases of RF.

Other schemes may be envisaged resulting in RF confinement.

The geometry of the device need not have a circular cross section. Elliptical, rectangular or irregular cross sections can be envisaged.

The inner component shown in FIG. 1 need not be concentric with the outer component.

The pitch of the travelling helical barrier described by the angle θ in FIG. 2 may vary along the length of the device. This effectively changes the speed at which ions are driven through the device by the travelling helical barrier with position along the device.

The driving force opposing the travelling DC helix may be a mass dependent force such as a pseudo potential force rather than a DC field. A pseudo potential driving force may be created by applying progressively higher amplitude of RF voltage with distance along the length of the device or by reducing the gap between the inner and the outer cylinder from the entrance end to the exit end.

In this case separation will be related to both the mobility and the mass to charge ratio of the ions.

It is possible to construct the device to produce the required fields in different ways than described in relation to the preferred embodiment. For example, the inner and outer cylinders may be concentric RF ring stacks with opposite phases of RF on adjacent rings. If these rings are themselves radially segmented then appropriate static and time varying DC potentials may be applied to the segments to produce the required fields.

Using this type of construction it is possible to apply a more traditional DC travelling wave to the device. The combination of a travelling DC helix opposed by a DC travelling wave may be used for enhanced mobility separation or mass separation as described in WO2008/071967.

Additionally using a multiply segmented ring stack a travelling pseudo potential helical barrier may be produced by altering the amplitude of RF applied to each segment in a time varying manner.

More than one travelling helical DC barrier may be simultaneously imposed over the length of the device creating more than one unique pathway for ions to travel down the device.

In another embodiment, this device may be used as a cylindrical differential ion mobility device (DIMS) device. In this embodiment the RF confining potential may be asymmetric or an additional asymmetric waveform may be applied to the RF confining electrodes between the inner and outer cylinder, In this embodiment the RF confining potential is applied between the complimentary spirals on the inner and outer cylinder such that the conductive strips on the inner cylinder are supplied with RF potential 180 degrees out of phase with the strips on the outer cylinder. All strips on the inner cylinder are the same phase and all strips on the outer cylinder are the same phase.

This results in dispersion of the ions in the radial direction between the inner and outer cylinders with respect to their differential ion mobility, Only ions within a specific band of differential ion mobilities will be contained within the device. Other ions will be lost to the electrodes of the inner or outer cylinder. By applying an additional DC voltage between the outer and the inner cylinders (compensation voltage) ions with different differential mobility can be arranged to be transferred though the device.

If, during differential ion mobility separation, ions are driven through the device by the helical travelling wave with no DC field, ions will only be separated in the radial direction. Ions may be introduced into this device as a continuous beam or as a pulse or packet of ions.

If DC field or a combination of DC and opposing helical travelling wave is used to drive ions through the device ions will separate radially with respect to their differential mobility and along the length of the spiral with respect to ion mobility.

The device can also be used in conjunction with another separation device (for example ion mobility or mass separator) or filter upstream or downstream of the device.

If a second IMS separation device is placed upstream of the device disclosed, the output of the first device can be synchronised to the changes in the speed of the helical DC travelling wave or the DC field strength to allow the IMS resolution to be optimised over a wide range of mobilities.

The embodiments disclosed may used in conjunction with each other or as multiple devices is series with ions passing from one device to another. For example, multiple devices constructs a shown for the planar spiral geometry in FIG. 6 may be stacked one on top of each other. Ions in the upper most spiral may be driven under a chosen set of conditions towards the centre of the spiral 17. The ions may then be directed, by a DC field for example, to the entrance of another spiral device directly below the first and separation of ions can continue down this second spiral. If the entrance to the second device is also at the centre of the spiral of the second device the direction of the field and the direction or rotation of the spiral barrier are reversed. In the example shown in FIG. 16 the field E will act radially in the direction from the centre of the spiral to the outside. By stacking multiple devices in this way the resolution and range of mobility values over which can reside in the device can be increased.

The devices disclosed may be used to analyse both positive and negative ions simultaneously. If positive ions are introduced at one end of the device and negative ions are introduced at the opposite end of the device these ions will travel in opposite directions and exit the device at opposite ends. Positive ions will take will take a unique path through the device compared to negative ions because of the nature of the travelling DC barriers. It is possible to use this characteristic to populate the device with both positive and negative ions and control their interaction time by removing or reducing the DC barrier. In this way ion-ion interactions such as electron transfer dissociation ETD, Hydrogen deuterium exchange HDX, or charge reduction may be performed.

It is possible to trap both positive and negative ions using the embodiments of the travelling DC barrier described by arranging ions to be urged towards the centre of the device by barriers rotating or moving in opposite directions at either end of the device.

Although the present invention has been described with reference to the preferred embodiments, it will be understood by those skilled in the art that various changes in form and detail may be made without departing from the scope of the invention as set forth in the accompanying claims.

The invention claimed is:

1. Apparatus for separating ions according to one or more physico-chemical properties, wherein said apparatus is arranged and adapted to create an ion channel in which ions are confined in use and wherein said ions are caused to separate according to said one or more physico-chemical properties along an axis of said ion channel or along said ion channel towards a first end and wherein said apparatus is further arranged and adapted to move said axis of said ion channel or said ion channel away from said first end.

2. Apparatus as claimed in claim 1, wherein said ion channel is formed between: (i) a first DC voltage gradient, a first DC potential, a first electrostatic barrier, a first DC potential barrier or a first pseudo-potential; and (ii) a second moving DC potential barrier, a second moving electrostatic barrier, a second moving DC potential barrier or a second moving pseudo-potential barrier.

3. Apparatus as claimed in claim 1, wherein said ion channel comprises a DC barrier and said ions are urged along the DC barrier and wherein said apparatus is arranged and adapted to move said DC barrier such that ions are moved towards an entrance or exit of the apparatus.

4. Apparatus as claimed in claim 3, wherein said ions are urged along the DC barrier using an electric field or a component of an electric field in a direction along the DC barrier.

5. Apparatus as claimed in claim 1, wherein said axis of said ion channel or said ion channel is non-linear, helical, spiral or curved.

6. Apparatus as claimed in claim 1, wherein said axis of said ion channel or said ion channel is linear.

7. Apparatus as claimed in claim 1, wherein said ion channel comprises a DC potential well.

8. Apparatus as claimed in claim 1, wherein said apparatus comprises:
a first device arranged and adapted to cause ions to separate according to said one or more physico-chemical properties in a first direction or along said axis of said ion channel or along said ion channel with a velocity which is substantially dependent upon said one or more physico-chemical properties.

9. Apparatus as claimed in claim 8, wherein said first device is arranged and adapted to apply or maintain a first electrostatic potential or force, a first DC potential or force, or a first pseudo-potential or force along at least a portion of said apparatus or along said axis of said ion channel or along said ion channel in order to cause ions to separate according to said one or more physico-chemical properties.

10. Apparatus as claimed in claim 1, wherein said physico-chemical property comprises ion mobility.

11. Apparatus as claimed in claim 1, wherein said physico-chemical property comprises differential ion mobility.

12. Apparatus as claimed in claim 11, wherein said apparatus comprises an inner cylinder and an outer cylinder, wherein said inner cylinder and said outer cylinder define an annular volume through which ions are transmitted in use; and
further comprising a device arranged and adapted to apply an RF confining potential to cause ions to disperse in a radial direction between said inner and outer cylinders with respect to their different ion mobility.

13. Apparatus as claimed in claim 1, wherein said physico-chemical property comprises mass or mass to charge ratio.

14. Apparatus as claimed in claim 1, wherein said apparatus comprises:
an inner cylinder and an outer cylinder, wherein said inner cylinder and said outer cylinder define an annular volume through which ions are transmitted in use; and
wherein one or more spiral or helical electrodes are arranged on a surface of said inner cylinder or on a surface of said outer cylinder.

15. Apparatus as claimed in claim 1, wherein said apparatus comprises:
a plurality of segmented planar electrodes; and
a second device arranged and adapted to apply DC voltages to said segmented planar electrodes so that one or more diagonal or inclined DC voltage barriers are translated along at least a portion of a length of said apparatus.

16. Apparatus as claimed in claim 1, wherein said apparatus comprises:
a plurality of inner ring electrodes and a plurality of outer ring electrodes, wherein said inner ring electrodes and said outer ring electrodes define an annular volume through which ions are transmitted in use, wherein said plurality of inner ring electrodes or said plurality of outer ring electrodes are radially segmented into a plurality of segmented electrodes.

17. A method of separating ions according to one or more physico-chemical properties comprising:
  causing ions to separate according to said one or more physico-chemical properties in a first direction with a velocity which is substantially dependent upon said one or more physico-chemical properties; and
  driving said ions in a second direction with a velocity which is substantially independent of said one or more physico-chemical properties, wherein ions are caused to separate according to said one or more physico-chemical properties in said first direction at substantially the same time that the ions are driven in said second direction so that a net effect is to extend a path length of ions.

18. Apparatus for separating ions according to one or more physico-chemical properties comprising:
  a plurality of electrodes;
  a first device arranged and adapted to cause ions to separate according to said one or more physico-chemical properties in a first direction with a velocity which is substantially dependent upon said one or more physico-chemical properties; and
  a second device arranged and adapted to drive said ions in a second direction with a velocity which is substantially independent of said one or more physico-chemical properties, wherein ions are caused to separate according to said one or more physico-chemical properties in said first direction at substantially the same time that the ions are driven in said second direction so that a net effect is to extend a path length of ions.

19. Apparatus as claimed in claim 18, wherein said first device is arranged and adapted to apply a first DC voltage gradient, a first DC potential, a first electrostatic barrier, a first DC potential barrier or a first pseudo-potential to cause ions to separate according to said one or more physico-chemical properties in said first direction.

20. Apparatus as claimed in claim 18, wherein said second device is arranged and adapted to provide a second moving DC potential barrier, a second moving electrostatic barrier, a second moving DC potential barrier or a second moving pseudo-potential barrier to drive ions in said second direction.

* * * * *